United States Patent [19]

Itho et al.

[11] Patent Number: 4,638,009

[45] Date of Patent: Jan. 20, 1987

[54] DERIVATIVES OF 3-PYRROLIDINOPROPIOPHENONE AND A PROCESS FOR PREPARATION THEREOF

[75] Inventors: Yasuo Itho, Katsuyamashi; Hideo Kato, Kentoku; Nobuo Ogawa, Katsuyamashi; Kagari Yamagishi, Katsuyamashi; Eiichi Koshinaka, Katsuyamashi; Hiroyuki Nishino, Katsuyamashi, all of Japan

[73] Assignee: Hokuriku Pharmaceutical Co., Ltd., Katsuyamashi Fukui, Japan

[21] Appl. No.: 573,862

[22] Filed: Jan. 25, 1984

[51] Int. Cl.⁴ .................. A61K 31/41; C07D 207/06
[52] U.S. Cl. ...................................... 514/428; 548/571
[58] Field of Search ................ 548/571; 424/274; 514/428

[56] References Cited

U.S. PATENT DOCUMENTS

| | | | |
|---|---|---|---|
| 3,151,124 | 9/1964 | Huebner | 548/571 X |
| 3,252,996 | 5/1966 | Huebner | 548/571 |
| 3,995,047 | 11/1976 | Morita et al. | 546/237 X |
| 4,277,474 | 7/1981 | Kohda et al. | 546/205 X |
| 4,465,678 | 8/1984 | Knops et al. | 514/237 |

FOREIGN PATENT DOCUMENTS

A-004000  9/1979  European Pat. Off. .
3019497  11/1981  Fed. Rep. of Germany .

OTHER PUBLICATIONS

The Merck Index, 10th ed., (1983), pp. 520 and 1363.

Primary Examiner—Joseph P. Brust
Attorney, Agent, or Firm—Gordon W. Hueschen

[57] ABSTRACT

Certain 4'-alkyl-2-methyl-3-pyrrolidinopropiophenones, acid addition salts thereof, their method of preparation, pharmaceutical compositions embodying the same, and a method of muscle relaxation therewith, are disclosed.

6 Claims, 1 Drawing Figure

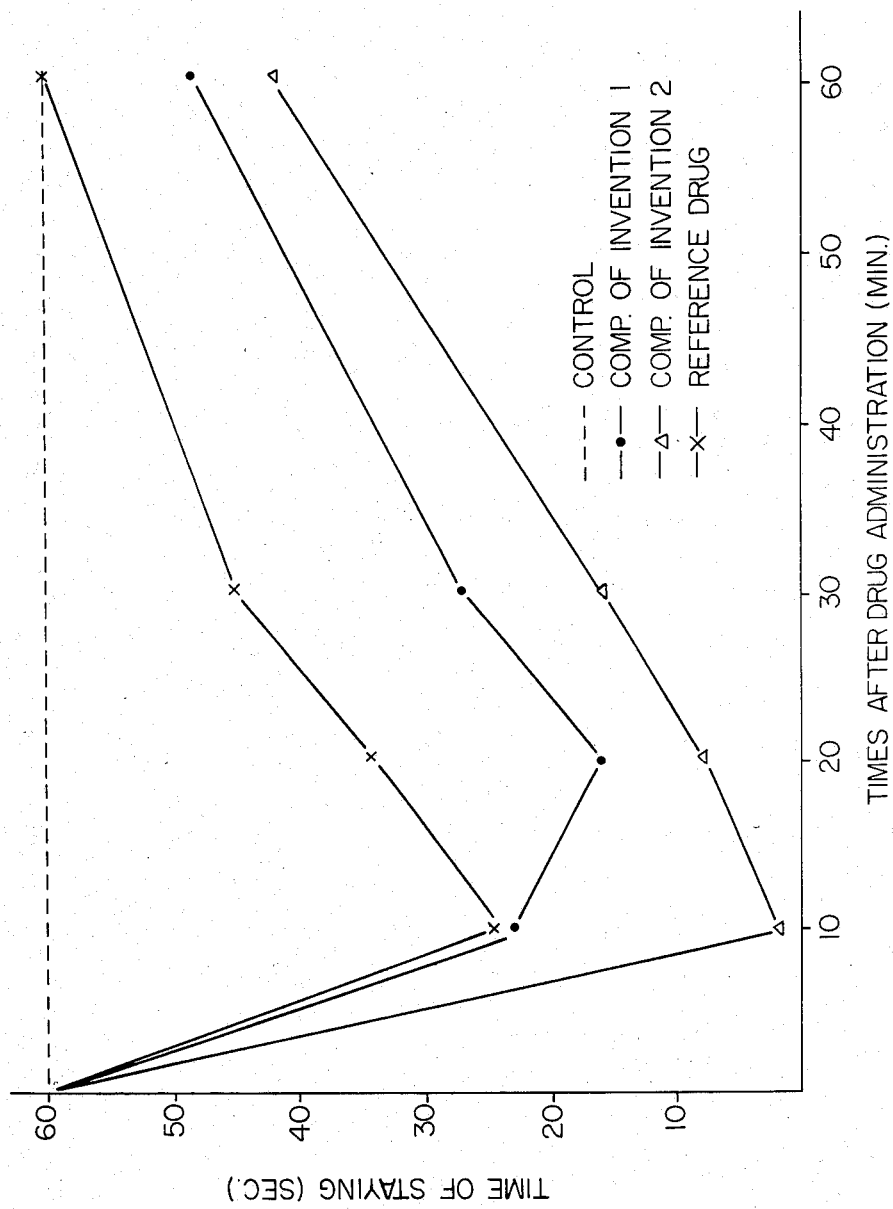

DERIVATIVES OF 3-PYRROLIDINOPROPIOPHENONE AND A PROCESS FOR PREPARATION THEREOF

FIELD OF THE INVENTION

This invention relates to novel derivatives of 3-pyrrolidinopropiophenone and the pharmaceutically acceptable acid addition salts thereof, which exhibit a potent activity on muscle relaxation and to a process for preparation thereof.

More particularly, this invention relates to the derivatives of 3-pyrrolidinopropiophenone represented by formula (I):

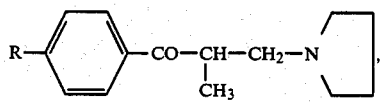
(I)

wherein R represents an ethyl-, propyl-, isopropyl-, butyl- and isobutylgroup or a cycloalkylgroup having 5-7 carbon atoms and the pharmaceutically acceptable acid addition salts thereof, as well as to a process for preparation thereof.

DESCRIPTION OF THE PRIOR ART

Hitherto, as a medicine having an activity on muscle relaxation, Tolperisone (generic name, Merck Index, 9th Edition, 9219) represented by formula (II):

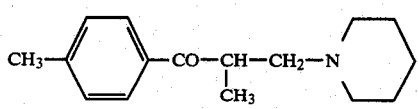
(II)

was on the market and been widely provided for clinical use in the treatment of muscular contractive and spastic paralysis.

Recently, for the purpose of improving the activity on muscle relaxation of Tolperisone, Eperisone (WHO Chronicle, 36(2), Proposed International Nonproprietary Names: List 47) represented by formula (III):

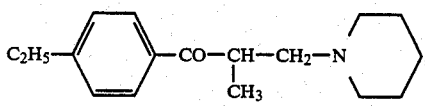
(III)

has been prepared and already clinically used.

Eperisone of formula (III) shows an improvement in muscle relaxation activity. However, Eperisone dose not show an improvement in toxicity and has just the same strong toxicity as Tolperisone. Further concerning the side effect, Eperisone causes hepatic and kidney function disorder, while Tolperisone possesses only the hepatic functional disorder. Therefore, Eperisone is rather regressive compared to Tolperisone in respect to the unwanted side effects.

Tolperisone and Eperisone, as medicines which are commercially available, are not yet satisfactory.

SUMMARY OF THE INVENTION

As a result of extensive investigation on new compounds having a potent activity on muscle relaxation, it has been found that the compounds of formula (I) have extremely weak toxicity and possess an effective activity on muscle relaxation as compared to those of formula (II) and (III), and thus this invention has been accomplished.

DETAILED DESCRIPTION OF THE INVENTION

In the foregoing formula (I), examples of cycloalkylgroup shown by R are a cyclopentyl-, cyclohexyl- and cycloheptyl group.

The compounds represented by formula (I) can be converted into the corresponding pharmaceutically acceptable acid addition salts in a conventional manner and the base can be liberated from the so prepared acid addition salts, if necessary.

Examples of the pharmaceutically acceptable acid addition salts of the compounds represented by formula (I), are salts with a mineral acid, such as hydrochloric acid, nitric acid, sulfuric acid, hydrobromic acid, hydroiodic acid, phosphoric acid and the like, and with an organic acid, such as acetic acid, maleic acid, fumaric acid, citric acid, oxalic acid, tartaric acid and the like.

According to this invention, the novel derivatives of 3-pyrrolidinopropiophenone represented by formula (I) can be prepared by reacting a derivative of propiophenone represented by formula (IV):

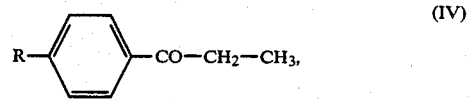
(IV)

wherein R is as defined above, with a formaldehyde and pyrrolidine represented by formula (V):

(V)

or a salt thereof in a solvent.

As a formaldehyde to be used for the preparation, formaldehyde itself, linear or cyclic polymers of formaldehyde, such as paraformaldehyde, trioxane and the like, can be employed. Pyrrolidine is used usually as a salt of a mineral acid such as hydrochloric acid, hydrobromic acid or nitric acid, whereas the pyrrolidine in the form of the free base is reacted in acid reaction medium by adding a sufficient amount of a mineral acid to the reaction mixure.

The mole ratio of the reactants can be chosen freely. However, 1 mol of pyrrolidine represented by formula (V) is reacted with at least 1 mol, preferably 1.1 moles, of a derivative of propiophenone represented by formula (IV) and at least 1 mol, preferably 1.5 moles, of formaldehyde, so that the pyrrolidine used can be eliminated from the reaction mixture, which should be submitted to an after treatment.

Solvent used in the process of this invention is an alcoholic solvent such as methanol, ethanol, propanol, isopropanol or the like, a nitroalkanic solvent, such as nitromethane, nitroethane or the like, or a lower alkyl ester of lower aliphatic acid, such as methyl acetate, ethyl acetate, ethyl propionate or the like. Preferably can be used a lower alkyl ester of a lower aliphatic acid.

The reaction can be carried out at a temperature between room temperature and the boiling point of the solvent used, preferably at the boiling point of the solvent.

The derivatives of propiophenone represented by formula (IV), which can be used as the starting materials for the process of this invention, are all known, and can be prepared in a manner as described, for example, in literature, Pharmazie, 24, 735(1969), Journal of the American Chemical Society, 78, 5899(1953), Annalen der Chemie, Justus Liebigs, 546, 273(1941), DBP 2059618, etc.

The thus prepared derivatives of 3-pyrrolidinopropiophenone represented by formula (I) and pharmaceutically-acceptable acid addition salts thereof exhibit in effective activity on muscle relaxation, inhibition of spinal reflex, nicotine-induced convulsion and oxotremorine-induced tremor and can be used extremely favorably as a medicine for treatment of spasmodic muscular contracture in diseases of kinesthetic origin such as low back pain, hernia of intervertebral dice, and osteoarthritis of the spine.

The compounds of this invention exhibit strong muscle relaxant activity with minimized side effects.

The high order of these activities of the active agent of this invention is evidenced by test in lower animals, representative of which are reported herein. A compound of this invention can be administered per os, e.g., in the form of pills or tablets, in which it may be present together with the usual pharmaceutical carriers, conventionally by compounding the compounds of this invention together with a customary carrier or adjuvant, such as talc, magnesium stearate, starch, lactose, gelatin, any of numerous gums, and the like. Thus, in their most advantageous form, the compositions of this invention will contain a non-toxic pharmaceutical carrier in addition to a active ingredient of this invention. Exemplary solid carriers are lactose, magnesium stearate, calcium stearate, starch, terra alba, dicalcium acacia, or the like.

Representative liquid carriers are peanut oil, sesame oil, olive oil, water, or the like. The active agents of this invention can be conveniently administered in such compositions containing active ingredient so as to eventually be within the dosage range illustrated hereinafter. Thus, a wide variety of pharmaceutical forms suitable for many modes of administration and dosages may be employed. For oral administration, the active ingredient and pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion, whereas, for parenteral administration, the composition may be in the form of a sterile solution or suppository.

The method of using the compounds of this invention comprises internally or externally administering the compound of this invention, preferably orally or parenterally and preferably admixed with the pharmaceutical carrier, for example, in the form of any of the above compositions, or filled into a capsule, to alleviate conditions to be treated and symptoms thereof in a living animal body. Illustratively, it may be used in an amount of about 1 to about 100 mg. per unit dose, preferably 30 to 80 mg. for an oral dose, while parenteral dosages are usually less and ordinarily about one-half of the oral dose. The unit dose is preferably given a suitable number of times daily, typically three times. The daily dose may vary depending upon the number of times given.

Naturally, a suitable clinical dose must be adjusted in accordance with the condition, age, and weight of the patient, and it goes without saying that the enhanced activities of the compounds of this invention, together with their reduced side effects, also make them suitable for wide variations, and the invention therefore should not be limited by the exact ranges stated. The exact dosage, both unit dosage and daily dosage, will of course have to be determined according to established medical principles.

The effective activity on muscle relaxation (rotating rod test), nicotine-induced convulsion and oxotremorine-induced tremor are shown in FIG. 1, Table 1 and 2 respectively, examples representing the potentiating pharmacological effect of the inventive compounds.

The acute toxicity has been determined are shown in Table 3, wherein as a reference compound, Eperisone, a marketed product, represented by formula (III) is used.

TEST COMPOUNDS

Compound of Invention 1 (Example 3)

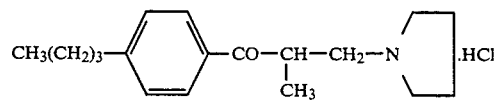

Compound of Invention 2 (Example 6)

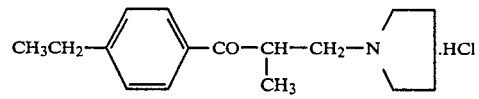

Reference Drug (Eperisone hydrochloride)

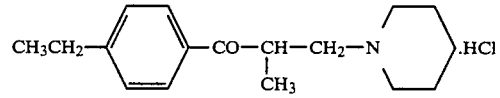

1. Activity on muscle relaxation
(rotating rod test)
Experiment:

Male ddY mice 5 weeks old were used with 10 animals in a group. The mice were tested previously by using a rotating rod of 3 cm in diameter at the rate of 10 r.p.m. and the mice which can stay on the rotating rod during more than 60 seconds were selected for the test. The compounds were administrated per os at a dose of 200 mg/kg and after 10, 20, 30 and 60 minutes of drug administration the mice were moved to the rotating rod. The times (seconds) of staying on the rod have been measured. It has been judged that the compound is effective, if the mice have fallen from the rod before staying 60 sec. The results are shown in the FIG. 1.

2. Activity on nicotine-induced convulsion
Experiment:

Male ddY mice 5 weeks old were used with 5 animals in a group. The compounds were administered per os at a dose of 25 mg/kg. After 15 minutes of drug administration, Nicotine tartarate was administered intravenously at an amount of 3 mg/kg and the tonic convulsions and dead animals because of the convulsions have been measured. The effect of the compounds has been indicated by percentage of appearance of tonic convulsion and the mortality.

Results are shown in Table 1.

TABLE 1

| | Activity on nicotine-induced convulsion | |
|---|---|---|
| compound drugs | appearance of tonic convulsion (%) | mortality (%) |
| Compound 1 of this invention | 20 | 40 |
| Compound 2 of this invention | 40 | 60 |
| Reference Drug | 60 | 100 |
| Control | 100 | 100 |

3. Effect on oxotremorine-induced tumor

Experiment:

Male ddY mice 5 weeks old were used with 5 animals in a group. The compounds were administrated per os at a dose of 100 mg/kg and after 15 minutes oxotremorine was intraperitoneally administered at dose of 1 mg/kg. The strength of the induced tremor was observed by the method of Suzuki et al (Folia Pharmacologica Japonica, 83, 127(1983) and scored up with passage of time as follows:

0=absent, 1=very slight,
2=slight, 3=moderate,
4=severe, 5=lack of righting reflex.

The results are shown in Table 2.

TABLE 2

| | Effect on oxotremorine-induced tremor | | | | |
|---|---|---|---|---|---|
| | Score passage of time (min) | | | | |
| compound drugs | 5 | 10 | 15 | 20 | 30 |
| Compound 1 of this invention | 0 | 0.4 | 0.4 | 0.9 | 0.8 |
| Compound 2 of this invention | 0 | 0.4 | 0.3 | 0.4 | 0.4 |
| Reference Drug | 0 | 0.4 | 0.3 | 0.2 | 0 |
| Control | 3.2 | 3.2 | 3.1 | 2.7 | 2.4 |

4. Acute toxicity test

Male ddY mice 5 weeks old were used with 5 animals at a group. The compounds were administrated orally with each dosage. $LD_{50}$ was determined by the Probit method from dead animals dying within 7 days.

Results are shown in Table 3.

TABLE 3

| | Acute Toxicity |
|---|---|
| Compound | $LD_{50}$ (mg/kg) |
| Compound 1 of this invention | 520 |
| Compound 2 of this invention | 425 |
| Reference Drug | 332 |

It is clearly seen from the results above that the compounds of this invention exhibit potent activity on muscle relaxation and excellent activity on nicotine-induced convulsion as compared to the reference drug.

Further, the acute toxicity test shows that the compounds of the invention have a lower $LD_{50}$ value as compared with Eperisone. Therefore, it is clear that the compounds of the invention are very useful as a medicine for clinical usage because of the superior pharmacological effects and of the lower toxicity.

This invention will be described in detail with reference to the examples below:

EXAMPLE 1

4'-Propyl-2-methyl-3-pyrrolidinopropiophenone

To a solution of 5.00 g of 4'-Propylpropiophenone in 10 ml of isopropanol were added 3.00 g of pyrrolidine hydrochloride, 1.30 g of paraformaldehyde and 0.5 ml of 40% ethanolic hydrogen chloride, and the mixture was refluxed for 4.5 hours and evaporated. The residue was dissolved in aqueous hydrochloric acid and washed with ether. The aqueous layer was made alkaline with potassium carbonate and extracted with ether. The extract was washed with water, dried and evaporated. The residue was dissolved in ether and acidified with 40% ethanolic hydrogen chloride. The precipitate was filtered, washed with a mixture of ethanol and ether, and recrystallized from methyl ethyl ketone to give 1.50 g of hydrochloride of the desired compound as colorless needles, mp 151°–152°.

Analysis for $C_{17}H_{25}NO \cdot HCl$: Calculated %: C, 69.02; H, 8.86; N, 4.73; Found %: C, 68.75; H, 9.23; N, 4.64

EXAMPLE 2

4'-Isopropyl-2-methyl-3-pyrrolidinopropiophenone

To a solution of 10.00 g of 4'-isopropylpropiophenone in 80 ml of ethyl acetate were added 2.00 g of pyrrolidine and 2.50 g of paraformaldehyde. The mixture was acidified by the addition of gaseous hydrogen chloride and refluxed for 4 hours.

After cooling, the reaction mixture was extracted with water. The water layer was made alkaline with potassium carbonate and extracted with ethyl acetate. The extract was washed with water, dried and evaporated. The residue was dissolved in ethanol and acidified with 15% ethanolic hydrogen chloride. The solution was evaporated and the residue was washed with a mixture of acetone and ether and then recrystallized from methyl ethyl ketone to give 3.58 g of hydrochloride of the desired compound as colorless needles, mp 131°–133°.

Analysis for $C_{17}H_{25}NO \cdot HCl$: Calculated %: C, 69.02; H, 8.86; N, 4.73; Found %: C, 68.62; H, 9.01; N, 4.62

EXAMPLE 3

4'-n-Butyl-2-methyl-3-pyrrolidinopropiophenone

To a solution of 5.40 g of 4'-butylpropiophenone in 15 ml of ethyl acetate were added 3.00 g of pyrrolidine hydrochloride, 1.30 g of paraformaldehyde and 0.5 ml of 22% hydrogen chloride-ethyl acetate and the mixture was refluxed for 4.5 hours. After cooling, the reaction mixture was extracted with aqueous hydrochloric acid. The water layer was made alkaline with potassium carbonate and extracted with ether. The extract was washed with water, dried and evaporated. The residue was dissolved in ethanol and acidified with 40% ethanolic hydrogen chloride. The solution was evaporated and the residue was washed with isopropyl ether and then recrystallized from methyl ethyl ketone to give 2.93 g of hydrochloride of the desired compound as colorless scales, mp 116°–117°.

Analysis for $C_{18}H_{27}NO \cdot HCl$: Calculated %: C, 69.77; H, 9.11; N, 4.52; Found %: C, 69.51; H, 9.25; N, 4.55

EXAMPLE 4

4'-Isobutyl-2-methyl-3-pyrrolidinopropiophenone

A solution of 5.40 g of 4'-isobutylpropiophenone in 15 ml of ethyl acetate, 3.00 g of pyrrolidine hydrochloride, 1.30 g of paraformaldehyde and 0.5 ml of 22% hydrogen chloride-ethyl acetate were treated in the same manner as that described for Example 3 to give 3.53 g of hydrochloride of the desired compound which were recrystallized from methyl ethyl ketone as colorless scales, mp 127°–128°.

Analysis for $C_{18}H_{27}NO.HCl$: Calculated %: C, 69.77; H, 9.11; N, 4.52; Found %: C, 70.13; H, 9.51; N, 4.66

EXAMPLE 5

4'-Cyclohexyl-2-methyl-3-pyrrolidinopropiophenone

A solution of 5.10 g of 4'-cyclohexylpropiophenone in 15 ml of ethyl acetate, 2.50 g of pyrrolidine hydrochloride, 1.30 g of paraformaldehyde and 0.5 ml of 22% hydrogen chloride-ethyl acetate were treated in the same manner as that described for Example 3 to give 3.65 g of hydrochloride of the desired compound, which were recrystallized from a mixture of ethanol and ether as colorless needles, mp 186°–187°.

Analysis for $C_{20}H_{29}NO.HCl$: Calculated %: C, 71.51; H, 9.00; N, 4.17; Found %: C, 71.64; H, 8.86; N, 4.12

EXAMPLE 6

4'-Ethyl-2-methyl-3-pyrrolidinopropiophenone

To a solution of 6.80 g of 4'-ethylpropiophenone in 60 ml of ethyl acetate were added 1.50 g of pyrrolidine and 1.90 g of paraformaldehyde.

The mixture was acidified by the addition of gaseous hydrogen chloride and refluxed for 2 hours. After cooling, the reaction mixture was extracted with aqueous hydrochloric acid. The water layer was made alkaline with potassium carbonate and extracted with ethyl acetate. The extract was washed with water, dried and evaporated. The residue was dissolved in ethanol and acidified with ethanolic hydrogen chloride. The solution was evaporated and the residue was washed with ethyl acetate and then recrystallized from methyl ethyl ketone to give 3.00 og of hydrochloride of the desired compound as colorless needles, mp 152°–153°.

Analysis for $C_{16}H_{23}NO.HCl.\frac{1}{4}H_2O$: Calculated %: C, 67.12; H, 8.62; N, 4.89; Found %: C, 67.35; H, 8.65; N, 5.01

What is claimed:

1. A compound which is selected from the group consisting of 4'-ethyl-2-methyl-3-pyrrolidinopropiophenone and a pharmaceutically-acceptable acid addition salt thereof.

2. A compound of claim 1 which is 4'-ethyl-2-methyl-3-pyrrolidinopropiophenone hydrochloride.

3. Pharmaceutical composition suitable for muscle relaxation comprising an effective muscle-relaxant amount of 4'-ethyl-2-methyl-3-pyrrolidinopropiophenone or an acid-addition salt thereof together with a pharmaceutically-acceptable carrier.

4. Pharmaceutical composition suitable for muscle relaxation comprising an effective muscle-relaxant amount of 4'-ethyl-2-methyl-3-pyrrolidinopropiophenone hydrochloride together with a pharmaceutically-acceptable carrier.

5. A method of relaxing muscles in a subject in need thereof comprising the step of administering an effective muscle-relaxant amount of 4'-ethyl-2-methyl-3-pyrrolidinopropiophenone or an acid-addition salt thereof to the said subject.

6. A method of relaxing muscles in a subject in need thereof comprising the step of administering an effective muscle-relaxant amount of 4'-ethyl-2-methyl-3-pyrrolidinopropiophenone hydrochloride to the said subject.

* * * * *

UNITED STATES PATENT AND TRADEMARK OFFICE
CERTIFICATE OF CORRECTION

PATENT NO. : 4,638,009

DATED : January 20, 1987

INVENTOR(S) : Yasuo Itho, Hideo Kato, Nobuo Ogawa, Kagari Yamagishi, Eiichi Koshinaka and Hiroyuki Nishino It is certified that error appears in the above-identified patent and that said Letters Patent is hereby corrected as shown below:

Col. 3, line 13; "in" should read -- an --
Col. 3, line 35; "a" should read -- the --
Col. 4, line 51; "can" should read -- could --
Col. 4, line 53; "administrated" should read -- administered --
Col. 5, line 22; "administrated" should read -- administered --
Col. 5, line 47; "at" should read -- in --

Signed and Sealed this

Twenty-second Day of September, 1987

Attest:

DONALD J. QUIGG

Attesting Officer     Commissioner of Patents and Trademarks